United States Patent [19]

Villari

[11] 4,051,852
[45] Oct. 4, 1977

[54] ASPIRATING DEVICE

[75] Inventor: Frank K. Villari, Oak Park, Ill.

[73] Assignee: The Kendall Company, Boston, Mass.

[21] Appl. No.: 590,786

[22] Filed: June 26, 1975

[51] Int. Cl.$^2$ .............................................. A61M 1/00
[52] U.S. Cl. ................................ 128/278; 128/214 R; 128/214 B; 128/274; 137/512.3; 417/431
[58] Field of Search ................ 128/234, 235, 273–278, 128/247, 214 R, 214 B, 214 E, 214.4, 214.2, 349 BV; 417/431, 900; 137/240, 512.3, 515.7, 525.1, 525.3, 625.41, 604; 251/309; 27/24

[56] References Cited

U.S. PATENT DOCUMENTS

| | | | |
|---|---|---|---|
| 3,158,152 | 11/1964 | Bloom | 128/145.5 |
| 3,332,418 | 7/1967 | Brody | 128/214 R |
| 3,572,375 | 3/1971 | Rosenberg | 128/274 |
| 3,631,853 | 1/1972 | Burdette, Jr. | 128/278 |
| 3,923,065 | 12/1975 | Nozick et al. | 128/349 BV |

Primary Examiner—John D. Yasko
Assistant Examiner—Henry S. Layton
Attorney, Agent, or Firm—Powell L. Sprunger

[57] ABSTRACT

A device for aspirating body fluids comprising, a valve assembly having a first port to receive body fluids, a second port for passage of the body fluids from the valve assembly, and a passageway communicating between the first and second ports. The valve assembly has one-way valve means associated with the passageway to permit passage of body fluids from the first port to the second port and prevent passage of body fluids from the second port to the first port. The device has port means communicating with the passageway intermediate the valve means and first port, with the port means being normally closed to prevent contamination of the device, and being openable to permit passage of fluid through the port means to the first port.

21 Claims, 7 Drawing Figures

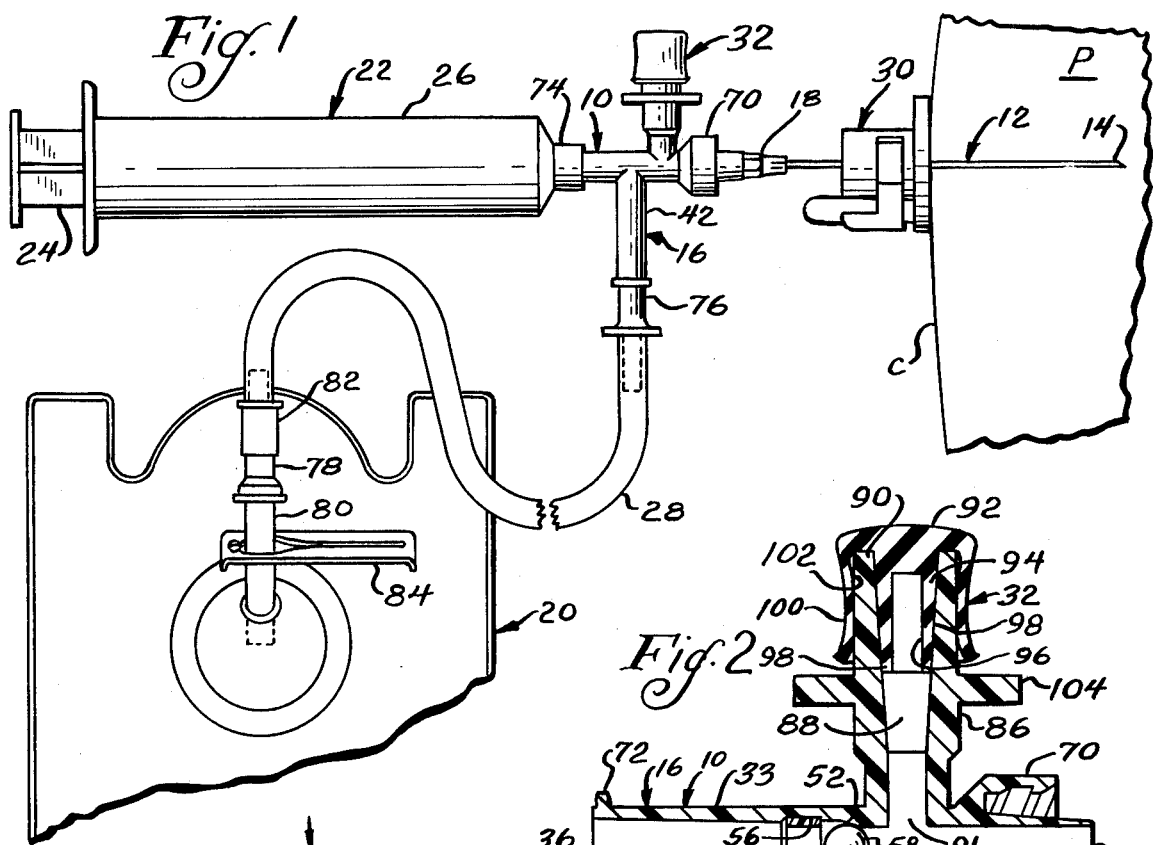

ASPIRATING DEVICE

BACKGROUND OF THE INVENTION

The present invention relates to medical devices, and more particularly to devices for aspirating body fluids.

During a thoracentesis procedure, a catheter or needle is positioned in the pleural cavity of a patient between the parietal and visceral layers of the pleura to remove a collection of fluid which may be in the cavity due to a number of reasons, such as emphysema. Various devices are provided for aspirating the fluid from the pleural cavity through the catheter or needle. During the aspirating procedure, an obstruction may occur in the catheter or needle (tube means) which prevents further aspiration, such as a blood clot which might block the tube means. In the past, it has been necessary to disconnect the device from the tube means, after which a saline solution is injected through the tube means to remove the block. Additionally, after the aspirating procedure has been properly completed, it is common to inject a medicant, such as an antibiotic, to prevent infection in the patient. Again, the device must be removed from the tube means to inject the medicant into the patient.

It will be apparent that the necessity to remove the device from the tube means during or after the aspirating procedure is both inconvenient and time consuming. Additionally, removal of the device from the tube means enhances the possibility that the otherwise closed system may become contaminated, resulting in possible harm to the patient.

SUMMARY OF THE INVENTION

A principal feature of the prevent invention is the provision of a device for aspirating body fluids from a patient in a simplified and safe manner.

The device of the present invention comprises, a valve assembly having a first port to receive body fluids, a second port for passage of the body fluids from the valve assembly, and a passageway communicating between the first and second ports. The valve assembly has one-way valve means associated with the passageway to permit passage of body fluids from the first port to the second port and prevent passage of body fluids from the second port to the first port. The device also has port means communicating with the passageway intermediate the valve means and first port.

A feature of the present invention is that the port means is normally closed to prevent passage of fluids through the port means and contamination of the device.

Another feature of the present invention is that the port means is openable to permit passage of fluid through the port means, the first port, and tube means connected to the first port for injecting a fluid into the patient.

A feature of the present invention is that fluids may be injected into the patient without the necessity for removal of the valve assembly from the tube means located in the patient.

Thus, another feature of the invention is that the fluids may be injected into the patient in a simplified manner while preventing contamination of the aspirating device.

Yet another feature of the invention is that in one embodiment the port means comprises a flexible plug which may be readily punctured in an asceptic manner by a needle.

Still another feature of the invention is that in another embodiment the port means comprises selectively openable valve means.

Further features will become more fully apparent in the following description of the embodiments of this invention and from the appended claims.

DESCRIPTION OF THE DRAWINGS

In the drawings:

FIG. 1 is a fragmentary elevational view of a device for aspirating body fluids from a patient;

FIG. 2 is a sectional view of a valve assembly in the aspirating device of FIG. 1;

FIG. 3 is a fragmentary sectional view of the valve assembly of FIG. 2 showing a needle punctured through port means in the assembly for injecting body fluids into the patient;

FIG. 4 is a plan view of a retainer ring for the valve assembly of FIG. 2;

FIG. 5 is a sectional view of another embodiment of port means for the valve assembly;

FIG. 6 is a perspective view of a valve member for the port means of FIG. 5; and FIG. 7 is a fragmentary sectional view showing a syringe as attached to the port means of FIG. 5 for injecting a fluid into the patient.

DESCRIPTION OF THE PREFERRED EMBODIMENTS

Referring now to FIG. 1, there is shown a device generally designated 10 for aspirating fluids from the pleural cavity of a patient P. The device 10 has a hollow needle (or catheter) generally designated 12 extending into the chest C of the patient P, the needle 12 having a tip 14 located in the pleural cavity of the patient. The device 10 also has a valve assembly generally designated 16 attached to a hub 18 of the needle 12, and a collection bag generally designated 20 communicating with the valve assembly 16. The device 10 also has pump means generally designated 22, such as a syringe, attached to the valve assembly 16, and having a plunger 24 for pumping body fluids from the patient.

As will be seen below, when the plunger 24 is withdrawn from a barrel 26 of the pump means or syringe 22, body fluids are removed from the patient through the needle 12 and the valve assembly 16 into a chamber in the syringe barrel 26. When the plunger 24 is pushed into the syringe barrel 26, the body fluids are ejected from the syringe chamber through the valve assembly 16 and a conduit 28 into a chamber in the bag 20 for collection therein. The device 10 may also include a positioning member 30 slidably received on and selectively positionable along the needle 12, such as the device described in U.S. Pat. Nos. 3,765,420 and 3,783,876, assigned to the assignee of the present invention, to position the needle tip 14 at the desired location in the pleural cavity. The device 10 also has port means generally designated 32 to permit injection of a fluid through the valve assembly 16 and the needle 12 into the patient.

As shown in FIGS. 1 and 2, the valve assembly 16 has a body member 33 having a first port 34 to receive body fluids from the patient, a second port 36 for passage of the body fluids between the valve assembly 16 and the syringe 22, and a first passageway 38 communicating between the first and second ports 34 and 36 to permit passage of the body fluids from the first port 34 to the second port 36. The valve assembly 16 also has first one-way valve means 40 in the first passageway 38 to permit passage of body fluids from the first port 34 to the second port 36 and prevent passage of the fluids from the second port 36 to the first port 34. The valve assembly 16 has a side arm 42 having a second passageway 44 communicating between a third port 46 and the first passageway 38 at an opening 48 located intermediate the first valve means 40 and the second port 36. The valve assembly 16 also has second one-way valve means 50 located intermediate the third port 46 and opening 48 in the second passageway 44 to permit passage of body fluids from the second port 36 to the third port 46 and prevent passage of fluids from the third port 46 to the second port 36.

The first and second one-way valve means 40 and 50 may be of any suitable type, such as a flap valve or the ball valves, as shown. Thus, the body member 33 has an annular seat 52 located in the first passageway 38 intermediate the opening 48 and first port 34. A partially annular retaining ring 54, as shown in FIG. 4, may be flexed slightly, and snap-fit into an annular recess 56 in the first passageway 38 intermeditate the opening 48 and the valve seat 52, as shown in FIG. 3, with a ball 58 being located intermediate the retaining ring 54 and the seat 52. Accordingly, the ring 54 retains the ball 58 adjacent the seat 52 to permit selective closure of the valve means. When the plunger 24 is withdrawn from the syringe barrel 26, the ball 58 is drawn against the ring 54. In this configuration, the ball 58 is spaced from the seat 52, and body fluids are permitted to pass around the ball 58 in the passageway 38 and through a cutout 60 and the ring 54, as shown in FIG. 4. With reference to FIG. 3, when the plunger 24 is pushed into the syringe barrel 26, the ball 58 is moved against the valve seat 52, and the ball 58 sealingly engages against the valve seat 52 to prevent passage of fluid through the valve means 40, thus directing the fluids into the second passageway 44.

The second one-way valve means 50 may be of similar construction. The body member 33 may have a valve seat 62 located in the second passageway 44, and a similar retaining ring 64 snap-fit into an annular recess 66 located in the second passageway 44 intermediate the seat 62 and the third port 46, with a ball 68 being retained by the ring 64 adjacent the valve seat 62. Accordingly, when the plunger 24 of the syringe 22 is withdrawn from the syringe barrel 26, the ball 68 is moved against the valve seat 62 of the second valve means 50 to prevent passage of fluids through the second valve means 50 while body fluids are withdrawn from the patient through the first passageway 38. When the plunger 24 is pushed into the syringe barrel 26, the body fluids are directed into the second passageway 44 of the valve assembly 16 by the first valve means 40, as previously described. In this configuration, the ball 68 is spaced from the valve seat 62, and the body fluids pass around the ball and through the cutout of the retaining ring 64 for passage into the conduit 28 and the chamber of the collection bag 20. In this manner, the body fluids are pumped from the pleural cavity of the patient by the syringe 22 through the needle 12 and valve assembly 16 into the syringe barrel 26, after which the aspirated body fluids are ejected from the syringe barrel 26 through the valve assembly 16 and conduit 28 for collection in the chamber of the bag 20.

As best shown in FIGs. 1 and 2, the body member 33 of the valve assembly 16 may have an annular threaded flange 70 adjacent the first port 34 providing means for releasably attaching the hub 18 of the needle 12 to the valve assembly 16. Also, the valve assembly 16 may have an outwardly directed flange 72 adjacent the second port 36 which is receivable in a threaded flange 74 of the syringe 22 adjacent its tip, in order that the syringe 22 may be releasably attached to the valve assembly 16. In this manner, communication is established between the needle 12 and syringe chamber of the barrel 26 through the passageway 38 of the valve assembly 16.

The tube or conduit means 28 may have a first connector 76 at an upstream end receivable in the third port 46 of the valve assembly 16 to releasably attach the tube 28 to the valve assembly with a lumen in the tube in communication with the second passageway 44. Also, the bag 20 may have an adapter 78 communicating through a flexible tube 80 with the chamber of the collection bag 20. The tube 28 may have a second connector 82 at its downstream end receivable on the adapter 78 to releasably attach the tube 28 to the adapter 78 and establish communication between the lumen in the tube 28 and the chamber in the bag 20 through the adapter 78 and tube 80. As shown, the bag 20 may have a clip 84 to selectively close and open the flexible tube 80.

As best shown in FIG. 2, the port means 32 has a hollow extension 86 defining channel means or a channel 88 communicating between an outer end 90 of the extension 86 and the first passageway 38 at an opening 91 intermediate the first port 34 and first valve means 40. The port means 32 also has flexible plug means 92 closing and sealing the outer end 90 of the channel 88. The plug means 92 may be made of any suitable material, such as rubber. As shown, the plug means 92 may have an inner plug member 94 received in the outer end of the channel 88, and having a channel 96 extending from an inner end 98 of the plug member 94. The plug means 92 may also have an annular sleeve 100 extending over an outer surface of the outer end 90 of the extension 86, such that the outer end 90 of the extension 86 is received in an annular groove 102 intermediate the plug member 94 and the sleeve 100 to retain the plug means 92 in place on the outer end 90 of the extension 86. The extension 86 may also have an annular flange 104 extending outwardly from the extension 86 adjacent an inner end of the sleeve 100 to facilitate use of the plug means 92 during injection of fluids into the patient.

As previously discussed, if the needle 12 should become obstructed, for example by a blood clot, during aspiration of body fluids from the pleural cavity while using the device 10, or if it is desirable to inject a medicant, such as an antibiotic, into the pleural cavity of the patient after the aspirating procedure, the port means 32 of the device is used to perform the injection, as discussed below in connection with FIGS. 1 and 3. As shown, the tip 106 of a sterilized needle 108 may be passed through the plug means 92 and channels 96 and 88 to a location adjacent the first passageway 38. In this configuration, the desired solution may be injected by a syringe attached to the needle through the needle 108 into the passageway 38 of the valve assembly 16 and through the needle 12 into the pleural cavity of the patient. The syringe plunger may be utilized to position the ball 58 against the seat 52 of the first valve means 40 during this time. Accordingly, the injection of the solution into the pleural cavity of the patient may be accomplished without the necessity for removal of the valve assembly 16 from the needle hub 18, and may be accomplished without contaminating the closed system. When the injection procedure has been completed, the needle 108 may be removed from the plug means 92, after which the plug means 92 automatically closes and seals the puncture to maintain the device in a sterile condition. Thus, the injection may be made in a simple and safe manner at a desired point in the aspirating procedure.

Another embodiment of the port means 32 is illustrated in FIGS. 5-7, in which like reference numerals designate like parts. In this embodiment, the valve assembly 16 has port valve means 109 having a valve body member 110 extending from the body member 33 of the valve assembly 16. The body member 110 has an annular valve seat 112, a valve chamber 114 located adjacent the seat 112, and a channel 116 communicating between the chamber 114 and the first passageway 38 of the valve assembly 16 through an opening 118 intermediate the first one-way valve means 40, as shown in FIG. 2, and the first port 34 of the valve assembly 16. Referring to FIGS. 5-7, the valve means 109 also has a cylindrical valve member 120 located in the chamber 114 adjacent the seat 112, and biasing means 122, such as a helical spring, for urging the valve member 120 against the valve seat 112. As shown, the valve member 120 has an annular ring 124 sealingly engages against the valve seat 112, and an elongated slot 126 in an outer surface 128 of the valve member 120 for a purpose which will be described below. The valve member 120 may include a plurality of longitudinally extending ribs 142 on its outer surface to maintain the valve member 120 in its desired position within the chamber.

The body member 110 also has an extension 130 having a tapered port 132 communicating with the chamber 114. The extension 130 has an outwardly directed flange 134 receivable in a threaded flange 136 of a sterile syringe 138 adjacent its tip 140, in order that the syringe 138 may be releasably attached to the extension 130. As shown in FIG. 5, before the syringe is attached to the extension 130, the valve member 120 sealingly engages against the valve seat 112 to prevent passage of fluid between the chamber 114 and port 132. As shown in FIG. 7, after the syringe 138 has been attached to the extension 130, the syringe tip 140 contacts the outer surface 128 of the valve member 120, and forces the valve member 120 away from the valve seat 112. Thus, the solution may be ejected from the syringe 138 through the syringe tip 140, after which the solution passes through the slot 126 around the outer end of the tip 140, between the ribs 142 of the valve member 120 and the sides of the chamber 114, through the channel 116 and passageway 38 and through the needle 12 to the pleural cavity of the patient. In this manner, the solution may be readily injected through the valve assembly 16 into the patient without removal of the valve assembly from the needle. Moreover, when the syringe 138 is removed from the valve extension 130, the valve member 120 again seals against the valve seat 112 to maintain sterility in the device 10.

It will be understood that any suitable port means may be utilized in connection with the device of the present invention. Additionally, it will be understood that the port means may be placed on a separate adapter which may be attached or positioned between the valve assembly of the present invention and the needle or catheter. Accordingly, the term valve assembly is contemplated to include such a structure within the scope of the present invention.

The foregoing detailed description is given for clearness of understanding only, and no unnecessary limitations should be understood therefrom, as modifications will be obvious to those skilled in the art.

I claim:

1. A device for aspirating body fluids, comprising:
 a valve assembly having a first port to receive body fluids, a second port for passage of the body fluids from the valve assembly, a passageway communicating between the first and second ports, one-way valve means associated with the passageway to permit passage of body fluids from the first port to the second port and prevent passage of body fluids from the second port to the first port, a third port, a second passageway communicating between the third port and the first passageway intermediate said valve means and second port, and second one-way valve means associated with the second passageway permitting passage of body fluids from the first passageway to the third port and preventing passage of fluids from the third port to the first passageway;
 port means communicating with the passageway intermediate said valve means and first port, said port means being normally closed to prevent contamination of the device, and being openable to permit passage of fluid through the port means to the first port; and
 pump means communicating with said second port for aspirating the body fluids through the valve assembly.

2. The device of claim 1 including a collection bag connected to said third port.

3. The device of claim 2 including conduit means connecting said bag to the third port.

4. The device of claim 3 including means for releasably attaching the conduit means to said bag and said valve assembly.

5. The device of claim 1 wherein said valve assembly includes a seat in the second passageway, and in which the second valve means comprises, a retainer ring positioned in the second passageway intermediate said seat and the third port, and a ball positioned in the second passageway intermediate said seat and ring for releasably sealing against said seat.

6. The device of claim 1 in which said valve assembly includes a seat in the passageway intermediate said first and second ports, and in which said valve means comprises, a retainer ring positioned in said passageway intermediate said seat and second port, and a ball positioned in said passageway intermediate said seat and said ring for releasably sealing against said seat.

7. The device of claim 1 wherein the pump means comprises a syringe.

8. The device of claim 1 including means for releasably attaching the pump means to said valve assembly with the pump means in communication with said second port.

9. The device of claim 1 including tube means communicating with said first port.

10. The device of claim 9 including means for releasably attaching said tube means to the valve assembly with the tube means communicating with said first port.

11. The device of claim 1 wherein said port means comprises flexible plug means to receive a needle.

12. The device of claim 11 in which said valve assembly includes an extension having channel means communicating with said passageway intermediate said valve means and first port, and in which said plug means closes an end of said channel means.

13. The device of claim 12 wherein said plug means includes a plug member received in said channel means.

14. The device of claim 13 in which said plug member includes a channel extending from an inner end of the plug member.

15. The device of claim 12 in which said plug means includes a sleeve extending over an outer end portion of said extension.

16. The device of claim 1 wherein said port means comprises, port valve means communicating with said passageway intermediate the one-way valve means and first port, said port valve means being normally closed to prevent passage of fluid through the port valve means, and said port valve means being openable responsive to contact against the port valve means to permit passage of fluid through the port valve means.

17. The device of claim 16 in which the port valve means comprises, a body member having a seat and a chamber adjacent the seat, a movable valve member located in said chamber adjacent the seat, and means for biasing said valve member against the seat to releasably seal said seat.

18. The device of claim 17 wherein the biasing means comprises a helical spring.

19. The device of claim 17 wherein the valve member includes an elongated slot in a surface facing the seat, said slot being located intermediate the seat.

20. The device of claim 17 including pump means, and means for releasably attaching the pump means to said body member with the pump means in communication with said chamber.

21. The device of claim 20 wherein said pump means includes an extension for contacting an outer surface of said valve member when the pump means is attached to the body member to retract the valve member from the seat.

* * * * *